United States Patent [19]

Kane

[11] Patent Number: 5,022,521
[45] Date of Patent: Jun. 11, 1991

[54] FLEXIBLE MEDICAL IMPLEMENT UTILITY POUCH

[76] Inventor: Beverly A. Kane, 35 Copley Ter., Apt. 3, Springfield, Mass. 01107-1707

[21] Appl. No.: 519,174

[22] Filed: May 4, 1990

[51] Int. Cl.$^5$ .............................................. B65D 85/00
[52] U.S. Cl. .................................... 206/370; 206/818; 383/39
[58] Field of Search ............... 206/362, 363, 370, 372, 206/373, 438, 439, 523, 818; 383/38, 39

[56] References Cited

U.S. PATENT DOCUMENTS

| | | | |
|---|---|---|---|
| 3,187,903 | 6/1965 | Oltz | 383/38 |
| 3,741,376 | 6/1973 | Brown et al. | 206/818 |
| 4,210,244 | 7/1980 | Westrick | 206/370 |
| 4,361,231 | 11/1982 | Patience | 206/362 |
| 4,415,089 | 11/1983 | Ruffa | 206/370 |
| 4,561,543 | 12/1985 | Thompson | 206/523 |
| 4,793,483 | 12/1988 | Holmes | 206/438 |
| 4,796,790 | 1/1989 | Hamilton | 206/438 |
| 4,826,059 | 5/1989 | Bosch et al. | 206/818 |
| 4,904,520 | 2/1990 | Dumas | 206/439 |

FOREIGN PATENT DOCUMENTS 0005622 of 1892 United Kingdom .................. 383/39

Primary Examiner—Jimmy G. Foster
Attorney, Agent, or Firm—Leon Gilden

[57] ABSTRACT

A flexible pouch for medical implements is manufactured from a disposable material which can be easily sterilized and includes a plurality of pockets for holding forceps, scissors, and similar surgical tools. The pouch includes plastic loops for holding cords or medical tubing and a bendable aluminum strap designed to retain a rolled towel. Additionally, one or more sections of the pouch can be formed from several layers of material with a thin magnet positioned between the layers for the purpose of holding the tools firmly secured thereto after they have been removed from their individual pockets. Peel-off adhesive strips are disposed around one or more edges of the pouch to facilitate a secure engagement thereof with a supporting surface.

8 Claims, 4 Drawing Sheets

PRIOR ART

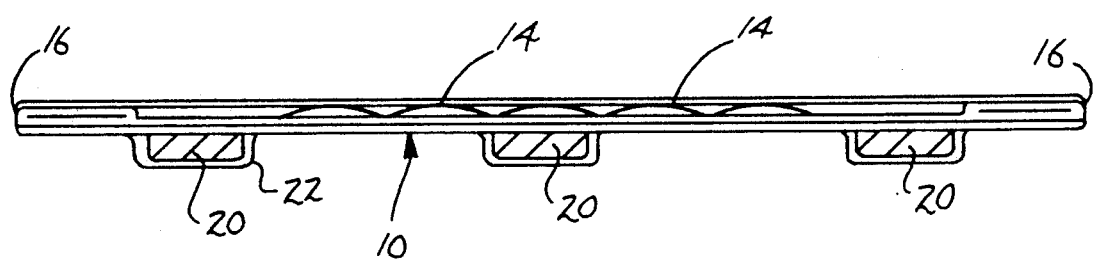
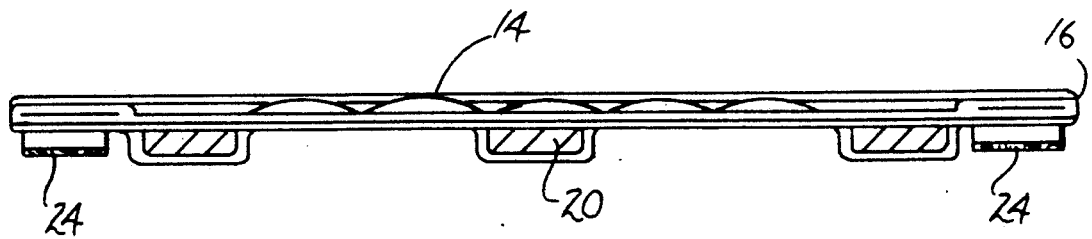

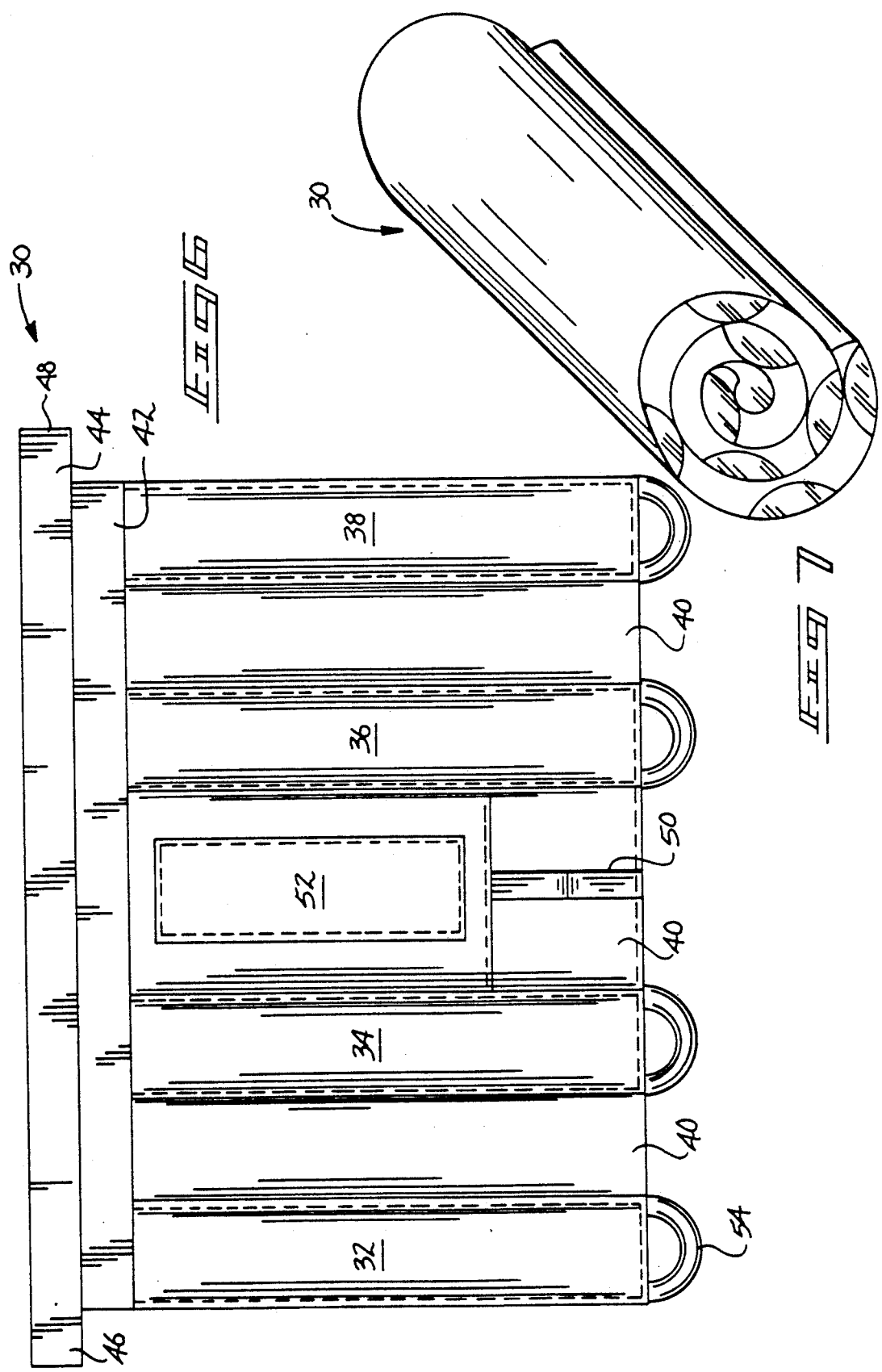

FLEXIBLE MEDICAL IMPLEMENT UTILITY POUCH

BACKGROUND OF THE INVENTION

1. Field of the Invention

The present invention relates to flexible tool kits, and more particularly pertains to a flexible implement holding pouch which may be used for holding implements associated with the medical profession.

2. Description of the Prior Art

The use of flexible tool holding pouches is known in the prior art. More specifically, flexible tool pouches heretofore devised and utilized for the purpose of storing and retaining tools during periods of non-use are known to consist basically of familiar, expected and obvious structural configurations, notwithstanding the myriad of designs encompassed by the crowded prior art which have been developed for the fulfillment of countless objectives and requirements.

More particularly, the flexible tool pouches is presently available in the art are substantially limited in both concept and function inasmuch as they are designed primarily as a tool storage means. The pouches are often constructed of materials which are rugged and cumbersome inasmuch as such materials add to the durability of the pouches per se, and little or no thought has been given to the idea of utilizing the pouches in an operable environment, e.g., such as during a medical operation. Such specialized pouches, if they were available, would have to be constructed from materials which could be easily sterilized and possibly, though not necessarily, reused. Further, provisions would have to be made for securing both the pouches and their associated tools in a fixed and stable position during a usage thereof. Apparently, such pouches are not presently available in the commercial market.

Therefore, it can be appreciated that there exists a continuing need for new and improved flexible tool pouches which can be used in specialized professions such as the medical field or the like. In this regard, the present invention substantially fulfills this need.

SUMMARY OF THE INVENTION

In view of the foregoing disadvantages inherent in the known types of flexible tool pouches now present in the prior art, the present invention provides an improved flexible tool pouch construction wherein the same can be used by the medical profession in an operating room environment. As such, the general purpose of the present invention, which will be described subsequently in greater detail, is to provide a new and improved flexible medical implement utility pouch which has all the advantages of the prior are flexible tool pouches and none of the disadvantages.

To attain this, the present invention comprises a flexible pouch for medical implements manufactured from a disposable material which can be easily sterilized and includes a plurality of pockets for holding forceps, scissors, and similar surgical tools. The pouch includes plastic loops for holding cords or medical tubing and a bendable aluminum strap designed to retain a rolled towel. Additionally, at least a center section of the pouch is formed from several layers of material with a thin magnet positioned between the layers for the purpose of holding the tools firmly secured thereto after they have been removed from their individual pockets. Peel-off adhesive strips are disposed around one or more edges of the pouch to facilitate a secure engagement thereof with a supporting surface.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out it various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved flexible medical implement utility pouch which has all the advantages of the prior art flexible medical implement utility pouches and none of the disadvantages.

It is another object of the present invention to provide a new and improved flexible medical implement utility pouch which may be easily and efficiently manufactured and marketed.

It is a further object of the present invention to provide a new and improved flexible medical implement utility pouch which is of a durable and reliable construction.

An even further object of the present invention is to provide a new and improved flexible medical implement utility pouch which is susceptible of a low cost of manufacture with regard to both materials and labor, and which accordingly is then susceptible of low prices of sale to the consuming public thereby making such pouches economically available to the buying public.

Still yet another object of the present invention is to provide a new and improved flexible medical implement utility pouch which provides in the apparatuses and methods of the prior art some of the advantages thereof, while simultaneously overcoming some of the disadvantages normally associated therewith.

Still another object of the present invention is to provide a new and improved flexible medical utility pouch which is particularly designed for retaining medical implements in an operating room environment.

Yet another object of the present invention is to provide a new and improved flexible medical implement utility pouch having a magnetic insert for retaining implements in secure engagement therewith.

Even still another object of the present invention is to provide a new and improved flexible medical implement utility pouch having cord and tubing retaining loops attached thereto.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a cross-sectional view of the pouch as viewed in the manner illustrated in FIG. 3.

FIG. 5 is an end elevation view of a modified embodiment of the present invention.

FIG. 6 is a top plan view of a third preferred embodiment of the present invention.

FIG. 7 is a perspective view of the invention illustrating the same in a rolled protective configuration with respect to the tools retained therein.

DESCRIPTION OF THE PREFERRED EMBODIMENT

Figure 1:
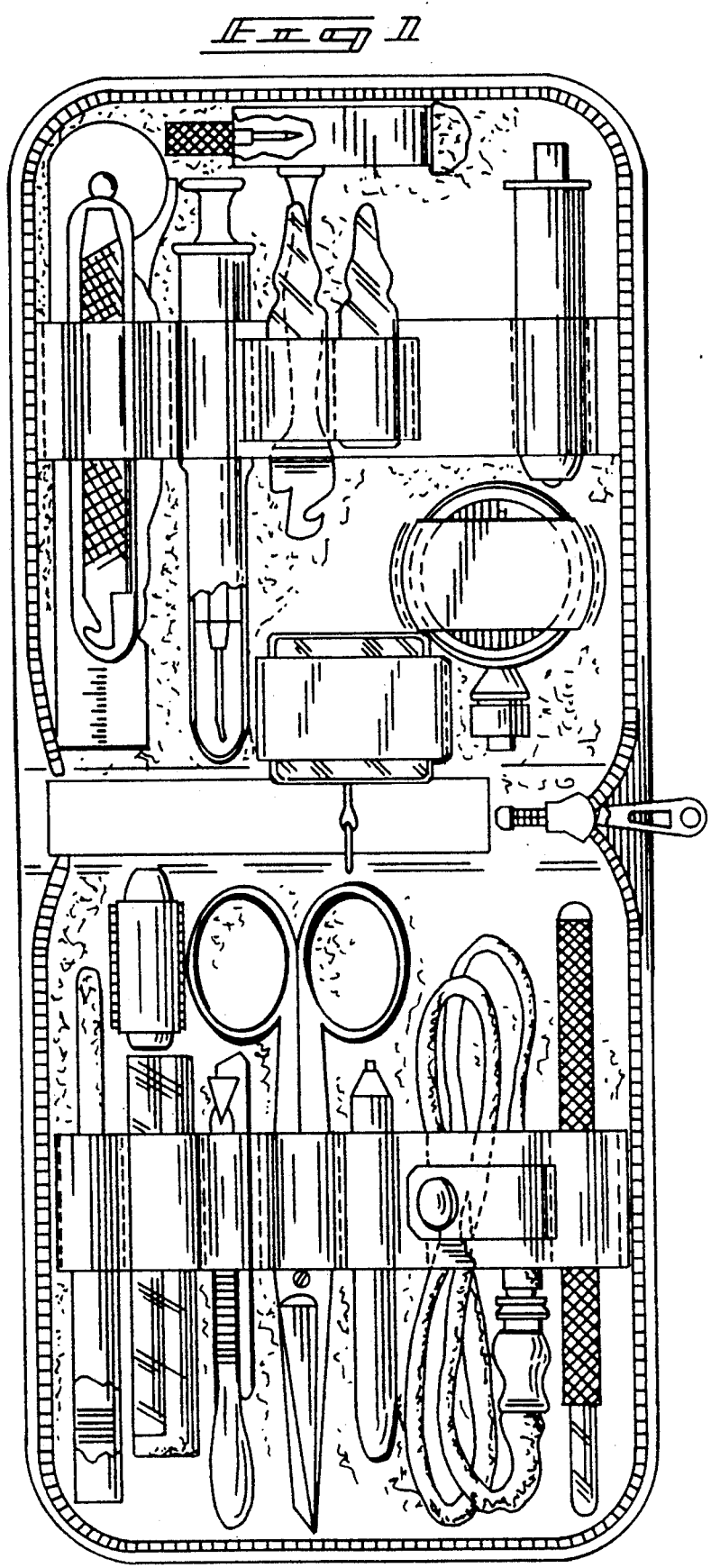
FIG. 1 is a top plan view of a prior art pocket medical kit.

With reference now to the drawings, a new and improved flexible medical implement utility pouch embodying the principles and concepts of the present invention and generally designated by the reference numeral 10 will be described.

Figure 2:
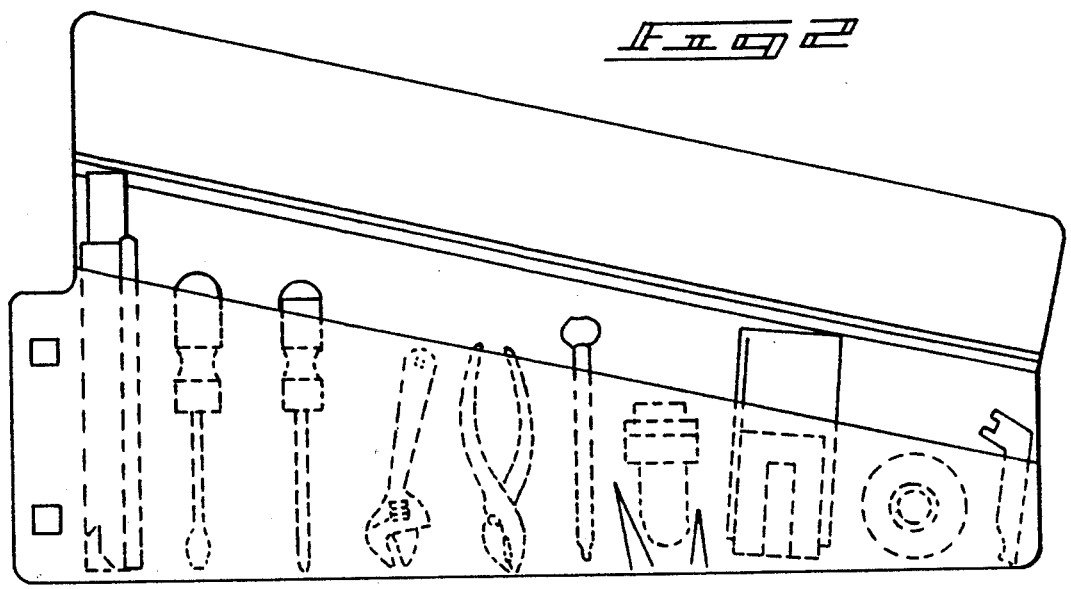
FIG. 2 is a top plan view of a prior art roll-up tool kit.

Initially, reference should be had to FIGS. 1 and 2 of the drawings wherein prior art configurations of interest are illustrated. More specifically, FIG. 1 represents a fitted pocket medical kit as shown in U. S. Pat. No. 2,804,969. This drawing is illustrative of the fact that it is known to provide protective storage pouches for medical instruments. By the same token, FIG. 2 of the drawings illustrates an automotive roll-up kit as shown in U.S. Pat. No 4,715,499. This tool kit is manufactured from flexible plastic material and has a plurality of compartments or open top pockets for receiving tools. When not being utilized, the kit may be rolled up and the remote ends are then fastened together by the use of mating Velcro pads. In effect, FIGS. 1 and 2 of the drawings illustrate the forefront of technology with resect to the providing of roll-up tool kits and pouches for medical implements.

Figure 3:
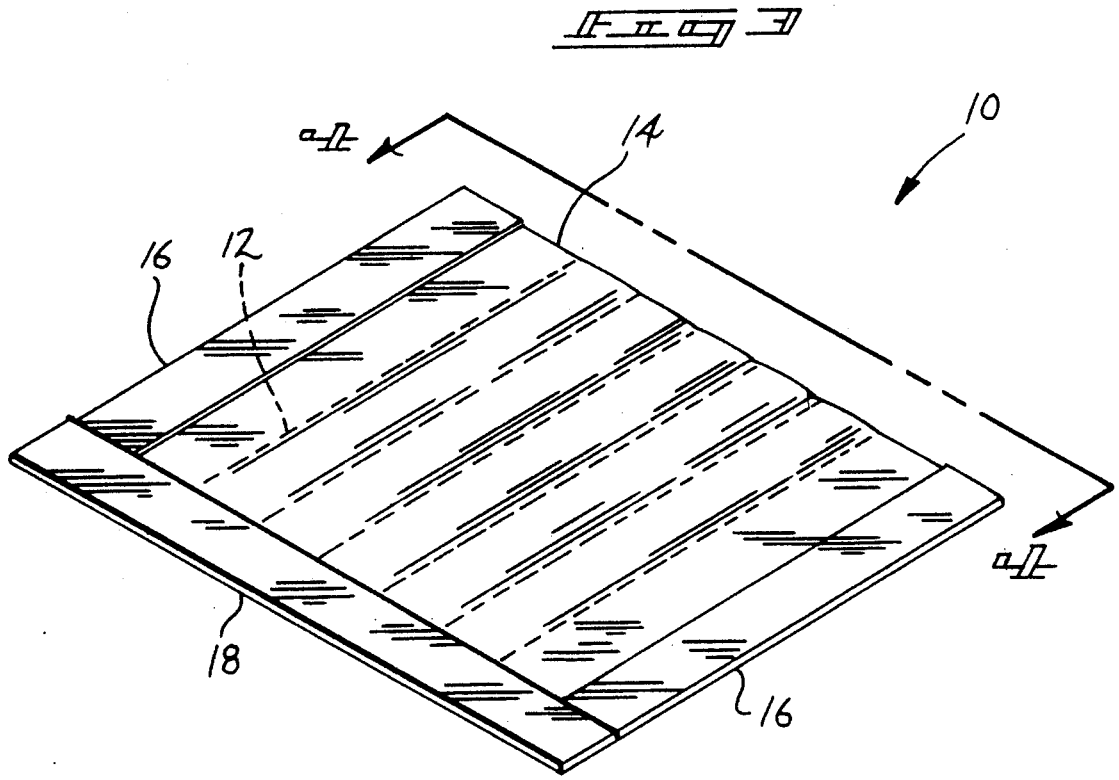
FIG. 3 is a perspective view of a first embodiment of the flexible medical implement utility pouch comprising the present invention.

FIG. 3 of the drawings illustrates a first embodiment of the present invention designated by the reference numeral 10 as aforementioned. In its basic form, the invention 10 should be manufactured from a double thickness of a disposable material, such as waterproof paper or thin foam sponge. The double layer construction permits the use of threaded seams 12 extending through both layers so as to form a plurality of pockets 14 for receiving various medical implements, such as polar forceps, scissors, suction devices, bovie pencils, and the like. The lateral and bottom edges 16, 18 respectively, are of a reinforced construction and are not specifically designed for the retention of tools.

FIG. 4 more particularly illustrates some of the novel features of the first embodiment of the invention 10. In this connection, it can be seen that a plurality of elongated magnets 20 may be selectively positioned at various locations within the folds of the pouch 10. Preferably, the magnets 20 are retained within material pockets 22 located on a bottom surface of the pouch. The magnets 20 serve two functions, i.e., to effect a magnetic attachment of the pouch 10 to a ferromagnetic support surface, such as a surgical tray or the like, and to effect a secure attachment of medical implements to the pouch——provided that the implements are also manufactured from ferromagnetic material. This latTr feature is particularly important during surgery since if a medical implement is dropped on the floor, it no longer possesses the sterile qualities required for performing a surgical operation. In this connection, the manufacture of a pouch from a disposable material such as waterproof paper or thin foam sponge, facilitates the sterilization thereof prior to its use in the sterile environment normally found in a medical operating room. A sterilized pouch 10 is then suitable for use as a support surface for the medical implements removed from the pouches 14 and as can now be appreciated, the magnets 20 function to retain the medical implements in position on the supporting surface of the pouch.

FIG. 5 of the drawings illustrates a further desirable feature which can be incorporated into the pouch 10. In this respect, peel-off adhesive strips 24 may be positioned around the edges 16, 18 of the pouch 10 to facilitates its secure attachment to a supporting surface. This is particularly useful when the supporting surface is not manufactured from a ferromagnetic material.

FIG. 6 of the drawings illustrates a second preferred embodiment of the invention which is generally designated by the reference numeral 30. The second embodiment illustrates a plurality of pockets 32, 34, 36, 38 which are particularly well suited for retaining polar forceps, scissors, bovie pencils, and suction tubing. Each of the pockets 32, 34, 36, 38 are separated by a flexible strip of material 40 which permits an easier appreciate that the conception, upon which this disclosure is rolling of the pouch 30 during periods of non-use. The pouch 30 is also provided with a top flap 42 which may be folded down over the pockets 32, 34, 36, 38 after medical implements are inserted therein, and a topmost peel-off adhesive strip 44 is also provided to facilitate an attachment of the pouch to a supporting surface. The ends of the adhesive strip 44 are provided with tabs or clips 46, 48 which are attachable together when the pouch is in a rolled condition.

An upstanding metallic aluminum loop 50 is also securely attached to the pouch 30 between the pockets 34, 36. The aluminum loop 50 is manually bendable so as to retain a rolled towel in position between the loop and the flexible strip 40 proximate thereto. Such rolled towels are useful in cleaning medical implements during use, and the metallic member 50 prevents the towel from becoming disengaged from the pouch 30. Effectively then, the pouch 30 operates as a tool in and of itself during the performing of a surgical procedure Also illustrated in FIG. 6 is a topmost totally sealed pocket 52 in which is retained a thin strip of magnetic material. As with the prior embodiment 10 of the invention, the magnetic material retained within the pocket 52 operates, when appropriate, to hold the pouch 30 in secure engagement with a ferromagnetic support surface and also operates to prevent medical implements from becoming disengaged from the pouch 30 when it is being utilized as a sterile surface.

Further illustrated in FIG. 6 are a plurality of semi-rigid plastic loops 54 which are attached to bottom edges of the pockets 32, 34, 36, 38. The loops 54 may comprise elongated cylindrical strips of plastic which are bent into a "U" shape and which are then sewn into the seams along the pockets 32, 34, 36, 38. The loops 54 then function to hold the pockets 32, 34, 36, 38 in a desired open shape, thereby to facilitate easy removal and insertion of the medical implements associated therewith, and the loops further function to retain cord or tubing in engagement with the pouch 30. More specifically, various cords and tubing may be required during surgical operations and quite frequently, such cords and tubing must be supported upon a surface which could also beholding the medical pouch 30. As such, the cords and tubing may be directed through the loops 54 or alternatively, flexible fasteners can be used to connect the cords and tubing directly to the loops 54 depending, of course upon the circumstances.

As to the manner of usage and operation of the present invention, the same should be apparent from the above description. Accordingly, no further discussion relating to the manner of usage and operation will be provided. In this regard, during periods of use, the medical implement pouches 10, 30 are opened and attached to a supporting surface to facilitate access to the implements contained therein, while during periods of non-use, the pouches 10, 30 may be rolled up to protect the medical implements in a manner best illustrated in FIG. 7.

In summary, the medical pouches 10, 30 possess substantial advantages over the prior art inasmuch as they are constructed from pliable disposable materials which are susceptible of gas sterilization or the like. The pouches 10, 30 can be easily secured to supporting surface by adhesive strips and tabs, as well as the magnetic plates 20 retained therein, and the loops 54 at the end of each pouch provide for the easy threading of cords and tubing therethrough. The pouches 10, 30 have pockets 14, 32, 34, 36, 38 which are deep enough to hold any type of medical implement, and if desired, identifying labeling can be provided on each pouch. The magnetic strips 20 disposed in each pouch 10, 30 are also useful for catching falling items or securing the implements being used, and the folded pouches are easily stored or transported.

What is claimed as being new and desired to be protected by LETTERS PATENT of the United States is as follows:

1. A new and improved medical implement retaining pouch comprising, flexible pouch means for storage of medical implements;

medical implement retaining pockets attached to said pouch means;

first securing means for selectively attaching said pouch means to a supporting surface; and second securing means for selectively attaching said pouch means to said supporting surface, and wherein said flexible pouch means is manufactured from a disposable material, and further including at least one semi-rigid loop for receiving cords and tubing, and wherein said at least one semi-rigid loop is positioned along a bottom edge of said flexible pouch means.

2. The new and improved medical implement retaining pouch as described in claim 1, wherein said disposable material is capable of being sterilized.

3. The new and improved medical implement retaining pouch as described in claim 2, wherein said disposable material comprises waterproof paper.

4. The new and improved medical implement retaining pouch as described in claim 2, wherein said disposable material comprises a thin foam sponge material.

5. The new and improved medical implement retaining pouch s described in claim 4, wherein said sterilization is accomplished by gas sterilization.

6. The new and improved medical implement retaining pouch as described in claim 1, wherein said first securing means comprises adhesives and said second securing means comprises at least one magnet.

7. The new and improved medical implement retaining pouch is described in claim 6, wherein said at least one magnet also functions to retain medical implements in engagement with said flexible pouch means.

8. The new and improved medical implement retaining pouch as described in claim 1, wherein said pockets are sewn to said flexible pouch means.

* * * * *